US006515742B1

(12) United States Patent
Ruprecht

(10) Patent No.: US 6,515,742 B1
(45) Date of Patent: Feb. 4, 2003

(54) DEFECT CLASSIFICATION USING SCATTERED LIGHT INTENSITIES

(75) Inventor: David John Ruprecht, St. Charles, MO (US)

(73) Assignee: MEMC Electronic Materials, Inc., St. Peters, MI (US)

( * ) Notice: Subject to any disclaimer, the term of this patent is extended or adjusted under 35 U.S.C. 154(b) by 133 days.

(21) Appl. No.: 09/723,847

(22) Filed: Nov. 28, 2000

(51) Int. Cl.[7] .......................... G01N 21/00; G01B 11/00
(52) U.S. Cl. ..................................... 356/237.4; 356/394
(58) Field of Search ......................... 356/237.1–237.4, 356/495, 446, 394; 250/562, 563, 570–572

(56) References Cited

U.S. PATENT DOCUMENTS

| | | | | |
|---|---|---|---|---|
| 4,423,331 A | * | 12/1983 | Koizumi et al. | 250/572 |
| 4,479,714 A | * | 10/1984 | Lehrer | 356/445 |
| 4,523,841 A | * | 6/1985 | Brunsting et al. | 356/73 |
| 4,598,997 A | * | 7/1986 | Steigmeier et al. | 356/237.1 |
| 4,744,663 A | * | 5/1988 | Hamashima et al. | 356/375 |
| 5,465,145 A | | 11/1995 | Nakashige et al. | |
| 6,256,093 B1 | | 7/2001 | Ravid et al. | |
| 6,271,916 B1 | * | 8/2001 | Marxer et al. | 356/237.3 |

FOREIGN PATENT DOCUMENTS

WO    WO 98/25131     6/1998

OTHER PUBLICATIONS

"Advanced Process Control: Soon to be A Must," *Semiconductor International*, Jul. 1999 by John Baliga, Associate Editor (11 pages). Available at http://www.semiconductor-.net/semiconductor/issues/issues/1999/jul99/docs/feature1.asp.

"Evaluation of the Yield Impact of Epitaxial Defects on Advanced Semiconductor Technologies," IEEE ISSM Conference, San Jose, California, Oct. 1999, by Randy Williams, Wayne Chen, Mustafa Akbulut, Niranjan Khasgiwale, Raj Persaud and Tom X. Tong (pp. 107–110).

"Evaluation of the yield impact of epitaxial defects on advanced IC technologies," micronmagazine.com MICRO, Jan., 2001, by Randy Williams, Robert Jacques, Mustafa Akbulut, and Wayne Chen (pp. 31–38).

"Evaluation of the Yield Impact of Epitaxial Defects on Advanced Semiconductor Technologies," 2000 IEEE/SEMI Advanced Semiconductor Manufacturing Conference, Randy Williams, Robert Jacques, Mustafa Akbulut, and Wayne Chen (pp. 1–7).

* cited by examiner

*Primary Examiner*—Michael P. Stafira
(74) *Attorney, Agent, or Firm*—Senniger, Powers, Leavitt & Roedel

(57) ABSTRACT

A system and method for detecting and classifying defects associated with the surface of semiconductor wafers, namely silicon wafers. An inspection device directs a laser light onto the wafer surface. Defects on the surface scatter the laser light into a plurality of photomultiplier tubes positioned to collect light scattered in distinct and separate collection angles. The photomultiplier tubes generate signals indicative of the estimated size of a defect causing the light to scatter based on the intensity of the light received by each respective photomultiplier tube. A processor compares the size estimations to a plurality of empirically determined power functions to identify the most likely type of the defect. The empirically determined power functions are derived from data obtained by manually inspecting a plurality of wafers. The size estimations are determined by comparing actual light intensities with calibration data obtained by scattering laser light off of known geometric objects, such as polystyrene latex spheres.

22 Claims, 12 Drawing Sheets

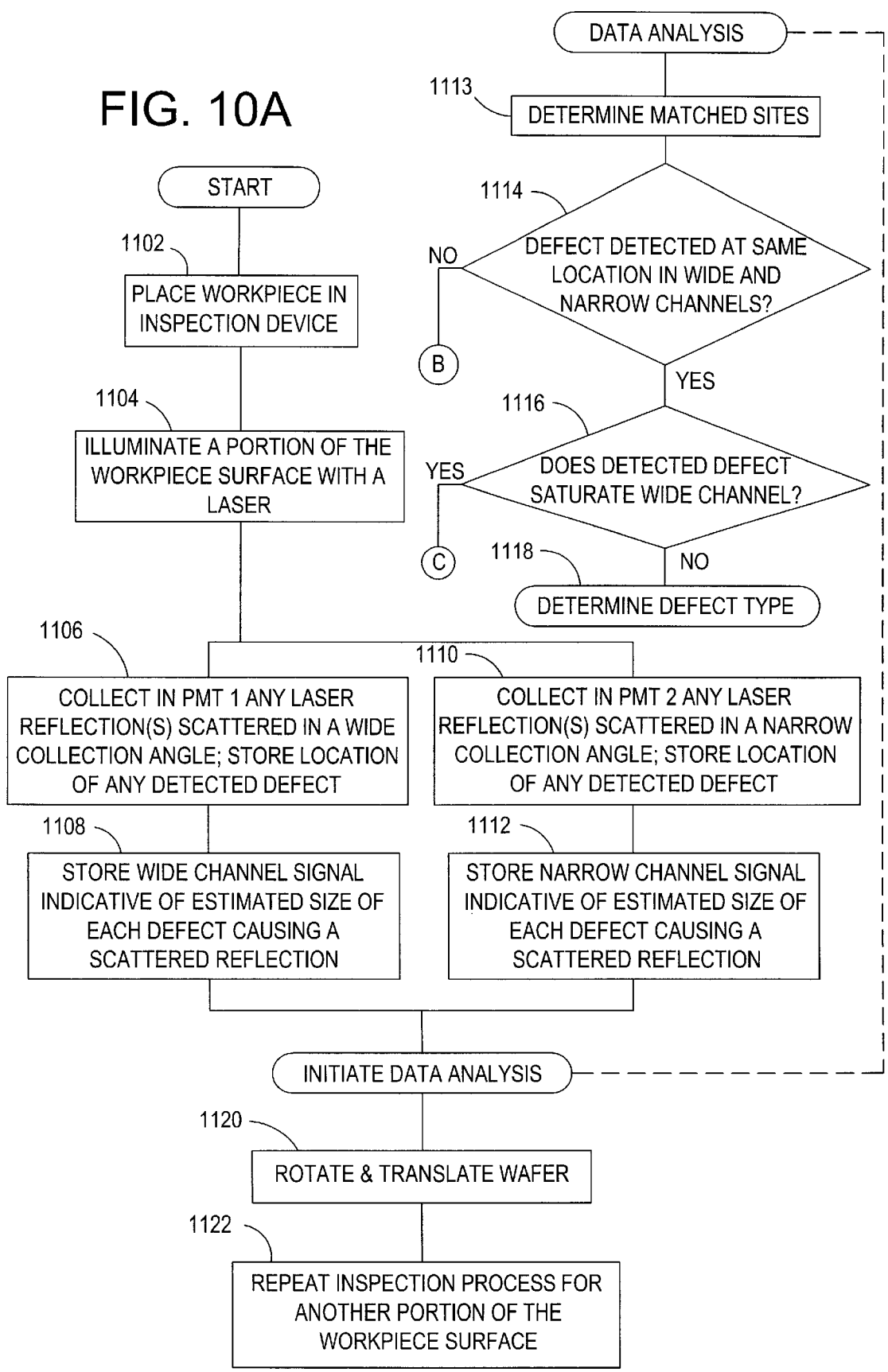

DEFECT CLASSIFICATION USING SCATTERED LIGHT INTENSITIES

BACKGROUND OF THE INVENTION

The invention relates generally to the identification and classification of surface defects on semiconductor wafers. In particular, the invention relates to a method and system for detecting and characterizing defects on silicon wafers with epitaxially grown films.

In the electronics industry, it is desirable to use defect free silicon wafers to manufacture electronic devices. It is now known to use surface inspection systems and equipment to inspect wafer surfaces to detect the presence of defects. One example of such an inspection system is the SP 1 wafer inspection system, available from KLA-Tencor.

Williams et al. describe one way to inspect silicon wafers with epitaxially grown films using the SP1 system. See Randy Williams et al. "Evaluation of the Yield Impact of Epitaxial Defects on Advanced Semiconductor Technologies," IEEE 1999 International Symposium on Semiconductor Manufacturing at 107–110, the entire disclosure of which is incorporated herein by reference. The SP 1 system sequentially illuminates the entire surface of a silicon wafer with a laser beam directed normal to the wafer surface. Typically, if the portion of the surface being illuminated is defect free, the light is reflected directly back and out of the system. Defects on the wafer surface, however, cause the beam to scatter and reflect at one or more angles. Any portion of the beam that is scattered back at an angle between 25 and 70 degrees is collected in a first photomultiplier tube (PMT 1), referred to also as the "wide channel." Any portion of the beam that is scattered back at an angle between 5 and 20 degrees is collected in a second photomultiplier tube (PMT 2), referred to also as the "narrow channel." Thus, the SP 1 collects information in two channels. Each channel is calibrated to a reference standard by using polystyrene latex (PSL) spheres/particles of known sizes, sometimes referred to as "PSL calibration." The intensity of the collected light in each channel provides a basis for estimating defect sizes by comparing the collected intensity with the calibrated intensity. Therefore, each channel provides an independent defect size estimation. The general operation of the SP 1 is described below with respect to FIGS. 1, 2, and 3.

As described by Williams et al., an algorithm may be used to compare the ratio of the defect sizes detected in each of the two channels. See Williams et al. at 108. Further, Williams et al. note that because both channels are similarly calibrated, particle defects result in a ratio approximately equal to 1. In other words, as shown by equation 1:

narrow channel size/wide channel size=1 (for particle defects)   [1]

the ratio of the estimated defect size as detected by the wide channel to the estimated defect size as detected by narrow channel is expected to be roughly 1. This results from the fact that the geometry of particle defects typically approximates a sphere—scattering light equally in both the narrow and wide directions.

Williams et al. also disclose that for epitaxial defects, the size estimations generated in the narrow and wide channels will typically differ because geometry of typical epitaxial defects does not approximate a sphere. As such, light scattered off of such defects will not ordinarily result in a size ratio of 1. Accordingly, a simple ratio may be used to classify detected defects as being either particles or non-particle defects. See Williams et al. at 108–09.

One important shortcoming of the simple ratio-based process disclosed by Williams is that it is limited to differentiating between particle and non-particle defects. In effect, Williams et al. classify all non-particle defects as epitaxial faults. In addition to particle defects and epitaxial faults, however, silicon wafers having epitaxially grown films may also have substrate related defects (e.g., defects located in the substrate that are not necessarily caused by the crystal pulling process). Thus, a wafer that is inspected using the inspection process described by Williams et al. may exhibit a significant defect that is not properly classified by that system and method.

In order to improve efficiency and throughput, it is important to know not only the presence of defects, but also the source and type of the defect. Cost conscious semiconductor wafer manufacturing requires attention to such information. See John Baliga, Advanced Process Control: Soon to be a Must, *Semiconductor International*, July 1999, available at http://www.semiconductor.net/semiconductor/issues/issues/1999/jul99/docs/feature1.asp, the entire disclosure of which is incorporated herein by reference. For example, particle defects may be removed by cleaning or re-cleaning the wafer. Defects associated with the epitaxial process may be the result of the recipe used. Thus, knowledge of the presence, size, and location of epitaxial defects can be used to improve and/or adjust the recipe to eliminate or reduce such defects. Finally, information regarding substrate related defects may be used to improve and/or adjust the crystal growth or wafering processes. It is therefore seen as to desirable to provide a semiconductor wafer inspection system that detects defects on the surface of the wafer, and classifies those defects into at least three categories—particle, epitaxially-related, or substrate related.

For these reasons, an improved method and system for identifying and classifying defects associated with semiconductor wafers is desired. Such a method and system improves manufacturing efficiencies by providing an automated source of data that may be used to identify defects and defect trend information.

SUMMARY OF THE INVENTION

The invention meets the above needs and overcomes the deficiencies of the prior art by providing an improved method and system for identifying and classifying defects associated with semiconductor wafers having epitaxial grown films. This is accomplished by identifying defect size information in a plurality of channels and comparing the identified defect size information to two or more curves. The curves define regions in which certain defect types tend to fall, thereby allowing defects to be classified on the basis of the size information obtained in the plurality of channels. The advantages of the present invention may be realized with minor software modifications to presently available inspection equipment.

Briefly described, a method of inspecting a workpiece surface embodying aspects of the invention includes providing a workpiece having a surface to be inspected. The workpiece surface is illuminated with an energy beam. The energy beam illuminates the workpiece surface at an angle of incidence and reflects off of the workpiece surface. A first collector collects a first portion of the energy beam reflected off of the workpiece surface at a first collection angle. A second collector collects a second portion of the energy beam reflected off of the workpiece surface at a second collection angle. A first size characterization of a defect associated with the workpiece surface is determined. A second size characterization of the defect associated with the workpiece surface is determined. A defect type characterization is determined by comparing the first and second size characterizations to a plurality of functions. The functions are selected to identify at least three defect types.

Another embodiment of the invention includes a method for inspecting a workpiece having a workpiece surface. The method includes placing the workpiece in an inspection chamber. The inspection chamber comprises a light generator for generating a light beam, a first beam collector, and a second beam collector. The light beam illuminates the surface of the workpiece at an angle of incidence. The light beam is reflected off of a defect associated with the surface of the workpiece. A first beam collector collects a portion of the reflected light beam that is reflected in a first collection angle. A second beam collector collects a portion of the reflected light beam that is reflected in a second collection angle. A first reflection intensity signal is determined. The first reflection intensity signal is representative of an intensity of the reflected light beam that is reflected in first collection angle. A second reflection intensity signal is determined. The second reflection intensity signal is representative of an intensity of the portion of the reflected light beam that is reflected in the second collection angle. The defect is associated with the surface of the workpiece is characterized by comparing the first and second reflection intensity signals to a plurality of power functions.

Yet another embodiment of the invention is a system for identifying a type of defect associated with a workpiece having a workpiece surface. A light generator generates a light beam. The light beam is directed to and reflected off of the defect. A first beam collector is positioned to receive a first portion of the light beam reflected off of the defect. The first portion is reflected off of the defect at a first collection angle. The first beam collector provides a first intensity signal having a parameter representative of an intensity of the first portion. A second beam collector is positioned to receive a second portion of the light beam reflected off of the defect. The second portion is reflected off of the defect at a second collection angle. The second beam collector provides a second intensity signal having a parameter representative of an intensity of the second portion. A processor determines the type of defect by comparing the first and second intensity signals to a plurality of functions. The functions are selected to identify at least three defect types.

Still another embodiment of the invention is a method of inspecting semiconductor wafer surfaces. The method includes locating a plurality of defects associated with the wafer surfaces. A first size associated with each of the plurality of defects is estimated. A second size associated with each of the plurality of defects is estimated. A plot is created of the first size estimation versus the second size estimation. The plurality of defects are analyzed to determine a defect type associated with each of the plurality of defects. The defect type associated with each of the plurality of defects is identified on the plot. At least two curves are located on the plot. The at least two curves substantially separate the plurality of defects into at least three different defect types.

Alternatively, the invention may comprise various other methods and systems.

Other objects and features will be in part apparent and in part pointed out hereinafter.

BRIEF DESCRIPTION OF THE DRAWINGS

FIGS. 10A–D are flow charts of a method of inspecting a semiconductor wafer according to the present invention. Corresponding reference characters indicate corresponding parts throughout the drawings.

DETAILED DESCRIPTION OF PREFERRED EMBODIMENTS

Figure 1:
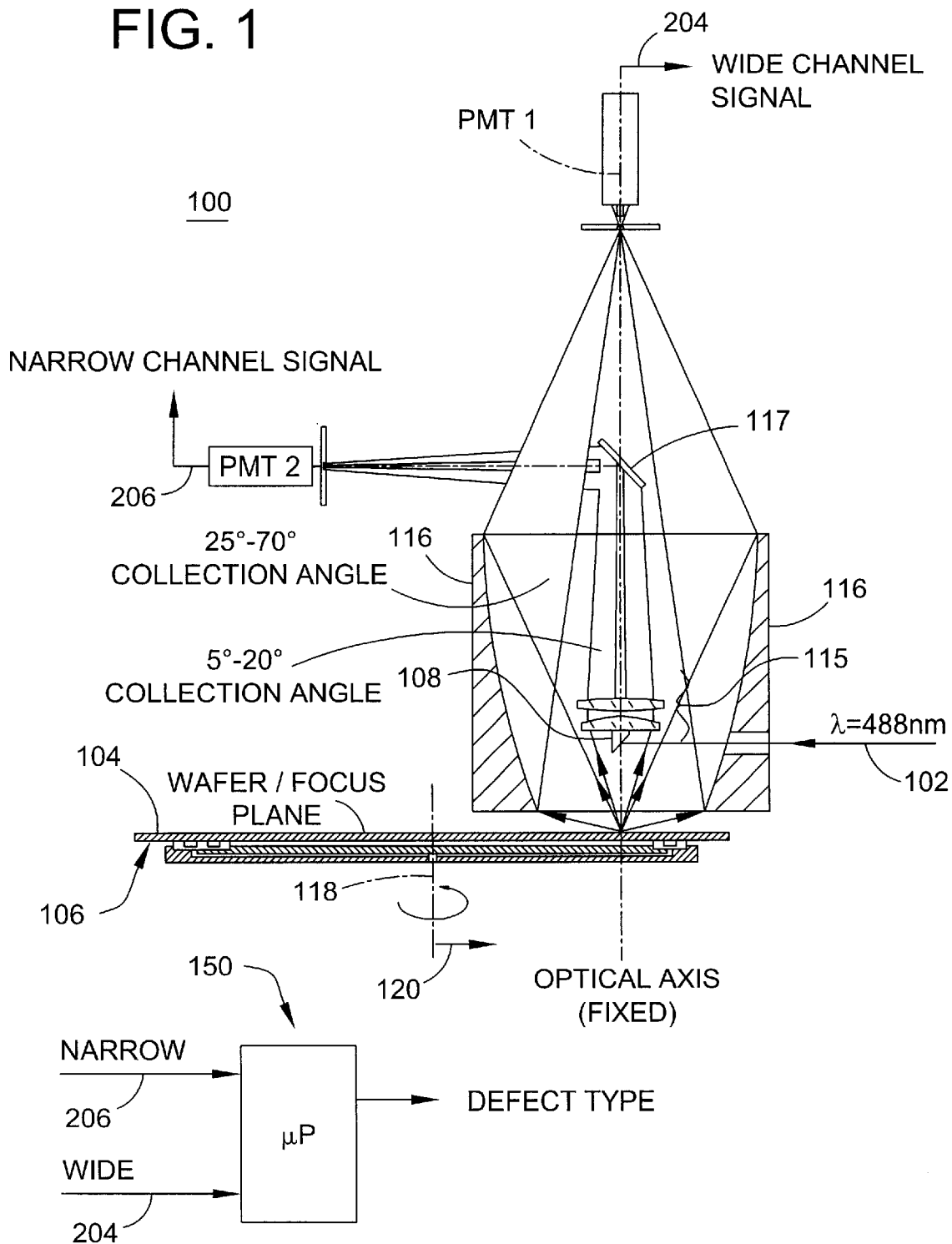
FIG. 1 is a schematic cross-sectional view of a wafer inspection device.
Figure 2:
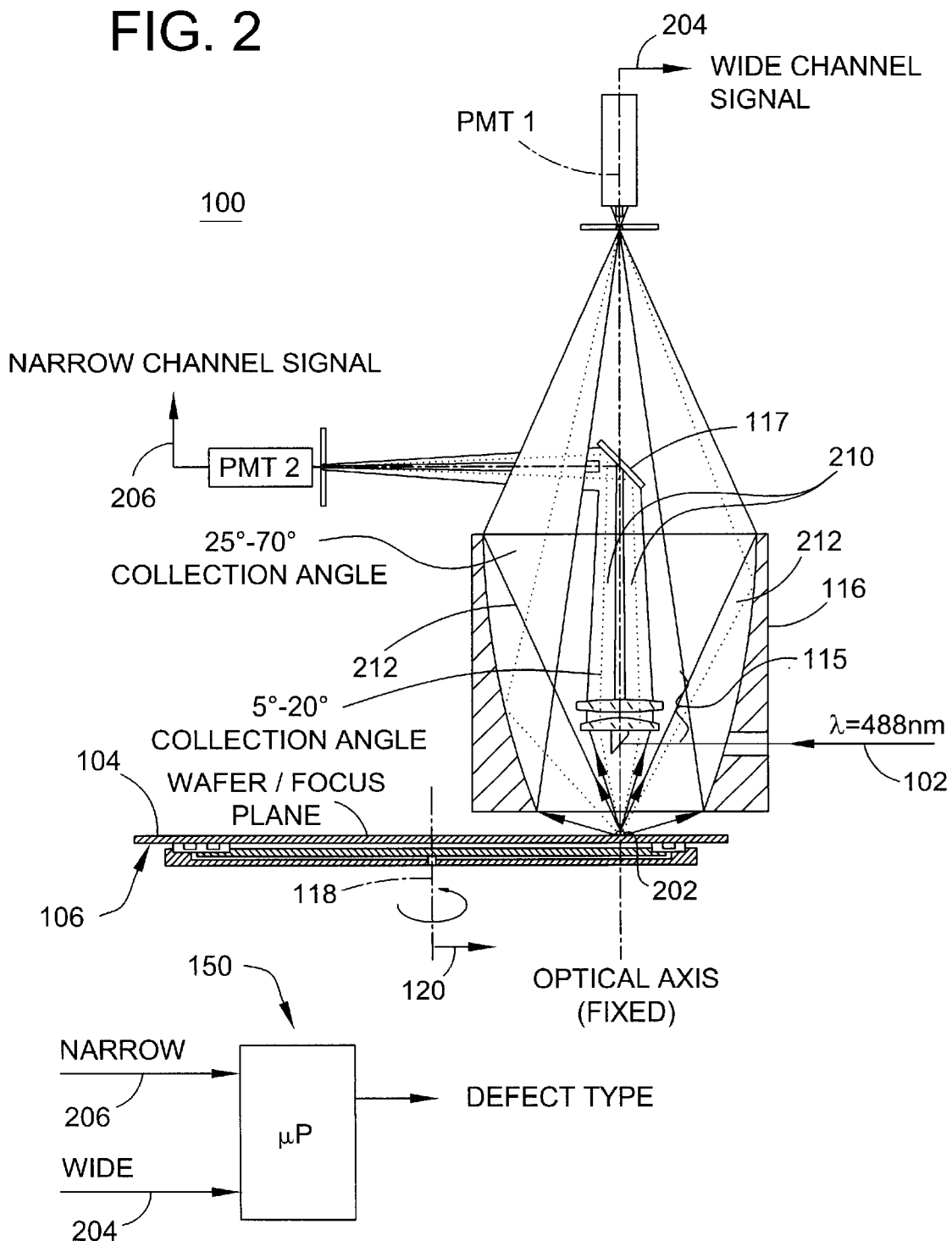
FIG. 2 is a schematic cross-sectional view of the wafer inspection device of FIG. 1 illustrating light reflected with different intensities and in different directions.

Referring now to the drawings, FIGS. 1 and 2 are schematic cross-sectional views of a semiconductor wafer surface inspection device 100, such as the SP 1 device currently available from KLA-Tencor Corporation and as described by Williams et al. As shown in FIGS. 1 and 2, an energy beam 102, preferably a laser beam having a 488 nm wavelength, is directed onto a portion of a surface 104 of a silicon semiconductor wafer 106 to be inspected. A mirror or similar laser reflector 108 causes the laser beam 102 to be directed onto the surface 104 at an angle of incidence normal to surface 104. Laser beam 102 is thereafter reflected off surface 104. As explained above, if the currently illuminated portion of surface to 104 is defect free, laser beam 102 reflects back at an angle less than five degrees from the angle of incidence. In other words, a defect free region of wafer surface 104 approximates a perfect reflector for inspection purposes and the laser light is reflected back out of the system. If, on the other hand, the region being illuminated contains a defect, laser beam 102 is scattered at various angles.

As shown in FIGS. 1 and 2, the inspection device 100 includes two photomultiplier tubes (PMT 1 and PMT 2) positioned to collect light scattered in two distinct collection angles. More particularly, PMT 1 provides a wide channel and collects light scattered between 25 and 70 degrees, as measured from the angle of incidence. A cylindrical elliptical mirror 116 focuses light scattered between 25 and 70 degrees into PMT 1. PMT 2 provides a narrow channel and collects light scattered between 5 and 20 degrees, as measured from the angle of incidence. A lens 115 and reflector 117 focus the light scattered between 5 and 20 degrees into PMT 2.

Preferably, the entirety of wafer surface 104 is sequentially scanned by the inspection device 100. While laser beam 102 remains focused, wafer 106 rotates about an axis of rotation 118, and translates about an axis of translation 120 such that wafer 104 is scanned in a spiral pattern. The system 100 is able to assign coordinate position information to any portion of wafer surface 104. Thus, the system 100 stores coordinate position information for any or all detected defects. It should be understood that it is possible to scan wafer surface 104 in different ways. The foregoing representing a preferred method of scanning surface 104 because it is employed by the SP 1.

FIG. 2 further illustrates how light scattered off of a defect 202 is collected in PMT 1 and PMT 2 to generate a wide channel signal 204 and a narrow channel signal 206. As shown therein, laser light 102 is directed toward surface 104 of wafer 106. As previously explained, any defect 202 present at that particular location causes light to scatter at various angles. The light scattered in a narrow angle 210 between 5 and 20 degrees is collected in to PMT 2 to produce the narrow channel signal 206. The light scattered in a wide angle 212 between 25 and 70 degrees is focused by the cylindrical elliptical mirror 116 into PMT 1 to produce the wide channel signal 204. Had there been no defect 202, no light would have been detected by either PMT 1 or PMT 2. Thus, when the portion of wafer surface 104 is defect free, the system produces no wide or narrow channel signals 204, 206.

The wide and narrow channel signals 204, 206 may be used to estimate the size of detected defect 202 by comparison to a known standard. As explained above, the inspection system 100 is preferably calibrated by scanning calibration/reference wafers (e.g., wafers previously determined to be defect free) having a plurality of PSL spheres of known diameter. The PSL spheres are located at various points on the wafer surface 104. Using a series of PSL spheres having different but known diameters, a calibration curve is obtained that allows the SP1 to report the size of detected defects in microns (or in $\mu$m PSL equivalent). Preferably, PMT 1 and PMT 2 have unique calibration curves. Thus, the wide channel signal is compared to the PMT 1 calibration data to provide a size estimation of a detected defect based on the intensity of the light reflected into, and collected by, PMT 1. Similarly, the narrow channel signal is compared to the PMT 2 calibration data to provide a size estimation of a detected defect based on the intensity of the light reflected into, and collected by, PMT 2. This process is repeated for each detected defect.

A processor 150 receives wide and narrow channel signals 204, 206 and determines the defect size and type based as a function of wide and narrow channel signals, 204, 206. The processor 150 may be integral to inspection device 100, or it may be a separate processor (e.g., a portable computer) that receives the intensity and defect location data from inspection device 100. Advantageously, processor 150 may be programmed to provide defect type information in real or near-real time, or it may be programmed to provide post-inspection data analysis.

Figure 3:
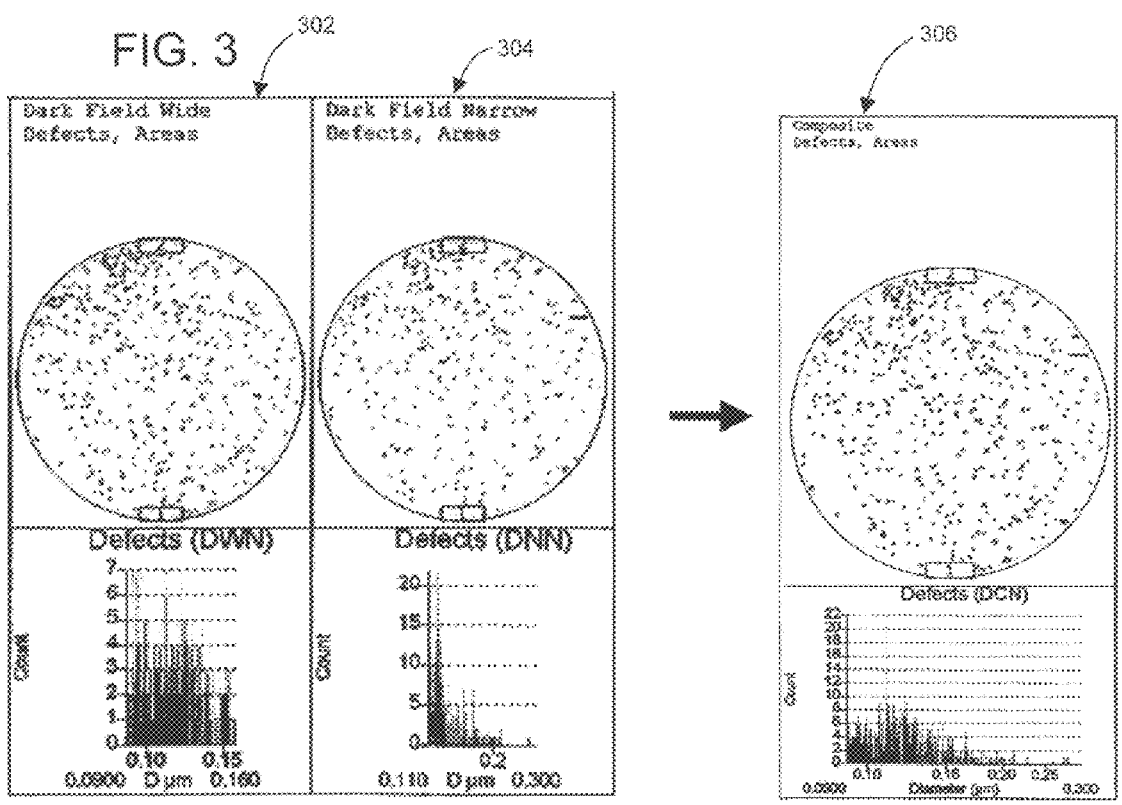
FIG. 3 is an exemplary plot of event maps illustrating the location of a plurality of scattering events detected by the wafer inspection device.

As shown in FIG. 3, defects detected in the wide channel (PMT 1) 302 and the narrow channel (PMT 2) 304 are mapped to locations on the wafer surface and size estimations are provided. This information is preferably combined, by inspection device 100 or by a separate processor using stored information, to provide a composite map 306. The SP 1 inspection device provides such the capability to generate the maps shown in FIG. 3.

Additional analysis preferably correlates the coordinate position of each detected defect such that a particular defect that is detected in both the wide channel 302 and the narrow channel 304 is mapped as a single point on the composite map 306. A correlated point—a defect detected at the same position in both the wide and narrow channels—may be referred to as a matched site or a matched defect site.

Figure 4:
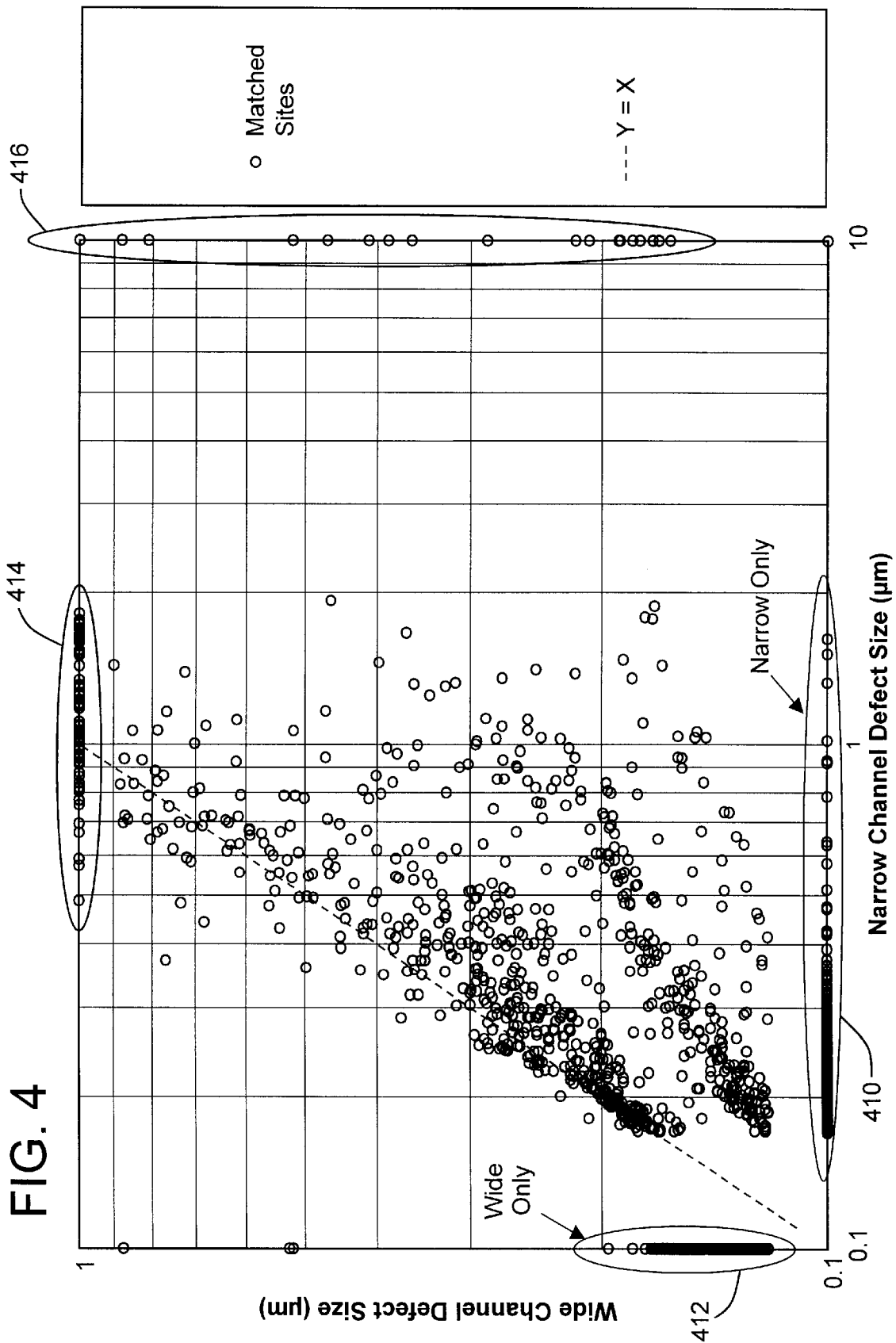
FIG. 4 is an exemplary plot of the size of a plurality of scattering events detected in the wide channel versus the size of the plurality of scattering events detected in the narrow channel.

FIG. 4 is an exemplary log—log plot of size data for matched defect sites. The vertical axis reflects defect size data obtained via the wide channel (PMT 1). The horizontal axis reflects defect size data obtained via the narrow channel (PMT 2). Unmatched defects are plotted on the respective axis. For example, effects that were detected only in the narrow channel are plotted on the horizontal axis, as shown by reference character 410. Likewise, defects that were detected only in the wide channel are plotted on the vertical axis, as shown by reference character 412. Further, any defect that was detected in only one channel is assigned a size of 0.1 $\mu$m for the non-detecting channel. If the detected defects had scattered the light in an ideal manner consistent with PSL spheres, all of the match sites would lie along the line Y=X. As shown in FIG. 4, however, such is not the case.

At this point it is instructive to note that large defects may reflect sufficient energy to saturate PMT 1 and/or PMT 2, thus making it difficult to accurately estimate defect size. As shown in FIG. 4, defects that saturate PMT 1 are given a size of 1 $\mu$m (see reference character 414); defects that saturate PMT 2 are given a size of 10 $\mu$m (see reference character 416).

Figure 5:
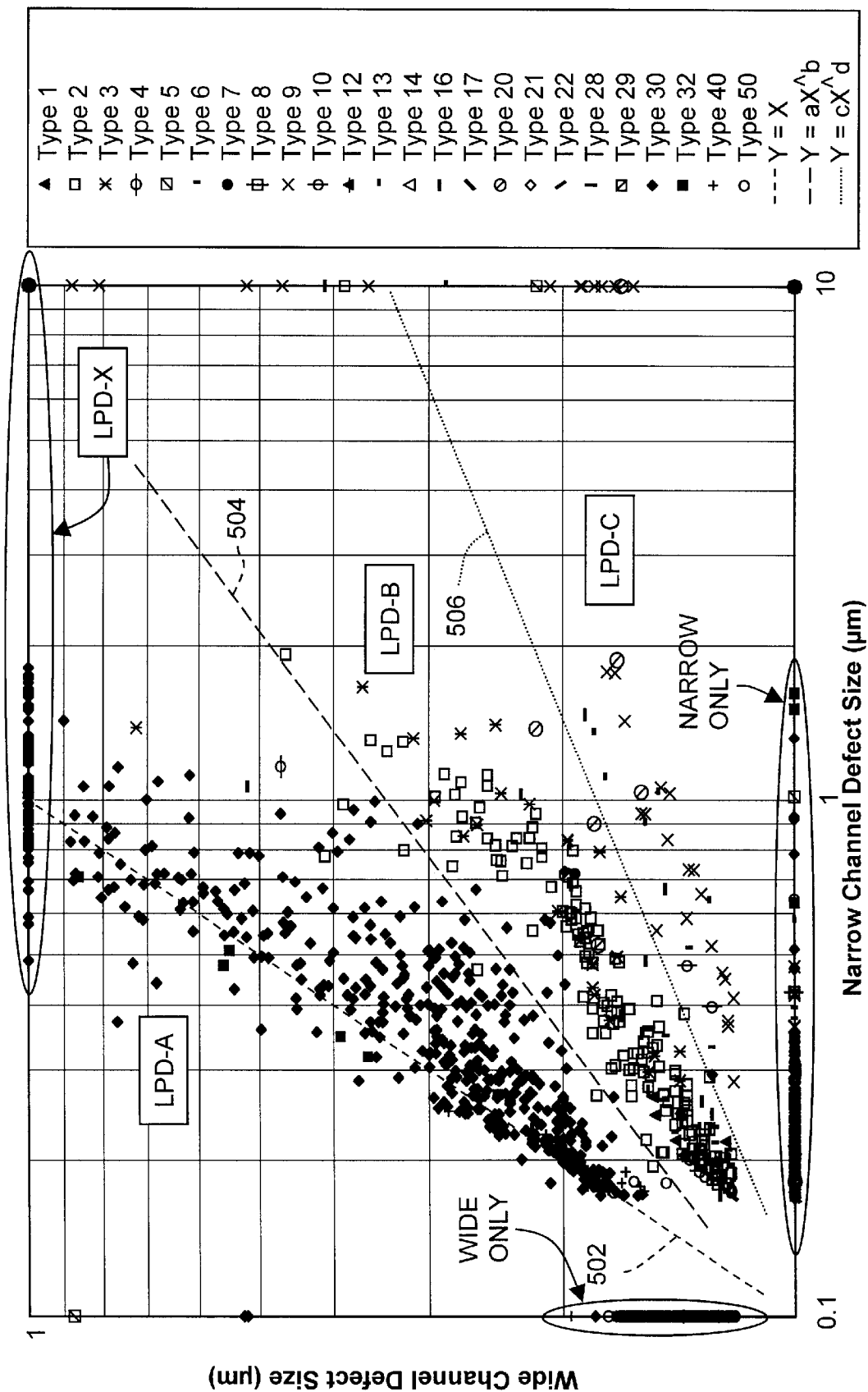
FIG. 5 is an exemplary plot as in FIG. 4 wherein the scattering events have been bit classified according to the invention by defect type, and wherein a plurality of power functions have been fit at empirically determined breaks between different broad categories of defect type.

FIG. 5 is an exemplary log—log plot of size data for matched defect sites. Further, unlike the plot of FIG. 4, FIG. 5 also identifies the defects by type. The defect location and size information plotted in FIG. 5 was obtained using the SP1 inspection device. The defect type information was manually obtained by visually inspecting the wafers. As shown in FIG. 5, there may be many different defect types. The defects identified, however, may be to grouped into several categories. In FIG. 5, the defects are grouped into four distinct and broad categories of types. First, the various types of particle defects are referred to in FIG. 5 as light point defects-type A (LPD-A). Second, defects originating with the epitaxial process (epi defects) are referred to in FIG. 5 as light point defects-type B (LPD-B). Third, substrate related defects are referred to in FIG. 5 as light point defects-type C (LPD-C). Finally, defects that saturated the wide channel (PMT 1) are referred to in FIG. 5 as light point defects-type X (LPD-X).

By analyzing light point defect data, such as the data plotted in FIG. 5, it was discovered that defect sizes identified in the wide and narrow channels tend to be grouped together by type in regions of the plot of FIG. 5. Unlike the prior art method and systems, such as those disclosed by Williams et al. which rely on a simple ratio (R=X/Y) to differentiate between particle defects and all other defects, the present invention unexpectedly and advantageously differentiates between particle defects, epitaxial defects, and substrate related defects. As shown in FIG. 5, analyzing a sizable number of wafers produces sufficient data such that natural breaks occur, defining distinct regions in which the LPD-A, LPD-B, and LPD-C categories of defects tend to fall. Using this information, a set of power functions 502, 504, 506 may be empirically determined to differentiate the defects by category of defect type (e.g., particle, epi defect, or substrate related). It should be noted that although the natural break points in the plot data make it preferable to empirically determine the power functions, different functions may be determined both empirically or by fitting a curve to the data by numerical methods. Equations 2–4 identify a preferred set of power functions 502, 504, 506, respectively.

$$Y=X \quad [2]$$

$$Y=aX^b \ a=0.34; \ b=0.51 \quad [3]$$

$$Y=cX^d \ c=0.18; \ d=0.27 \quad [4]$$

where a and c are coefficients and b and d are exponents; a, b, c, and d may be collectively referred to as parameters As can now be appreciated, once a suitable set of power functions has been determined, empirically or otherwise, the power functions may be employed with the inspection system 100, such as the SP1 and/or other processing equipment, to automatically classify defects detected during the inspection process. In other words, when a wafer is inspected, any detected defect may be classified by type in real or near-real time, thereby ha improving the overall efficiency and throughput of the wafer manufacturing process. This method has been successfully used to predict the nature of defects in silicon wafers having epitaxially grown films with defect sizes ranging from 0.12 $\mu$m PSL to 9 $\mu$m PSL, with a nominal accuracy in excess of 90%.

By comparing matched site data to regions defined by equations 3 and 4, it is possible to classify and associate defects into one or more of the defect types referred to herein as LPD-A, LPD-B, and LPD-C. For example, if a detected defect generates a particular size estimation in the narrow channel (which corresponds to the X axis in FIG. 5), that value may be input into equations 3 and 4. If the size estimation detected in the wide channel is greater than the value for Y that would be produced by equation 3 with the X value as determined in the narrow channel, the defect is most likely a particle defect (LPD-A). Similarly, if the size estimation detected in the wide channel is less than the value for Y that would be produced by equation 4 with the X value as determined in the narrow channel, the defect is most likely a substrate related defect (LPD-C). If, however, the size estimation detected in the wide channel falls between than the value for Y that would be produced by equations 3 and 4 using the X value as determined in the narrow channel, the defect is most likely an epitaxial defect (LPD-B). As discussed below, defects that saturate one or both channels may be more difficult to classify and treated as unknown defects (LPD-X).

Figure 6:
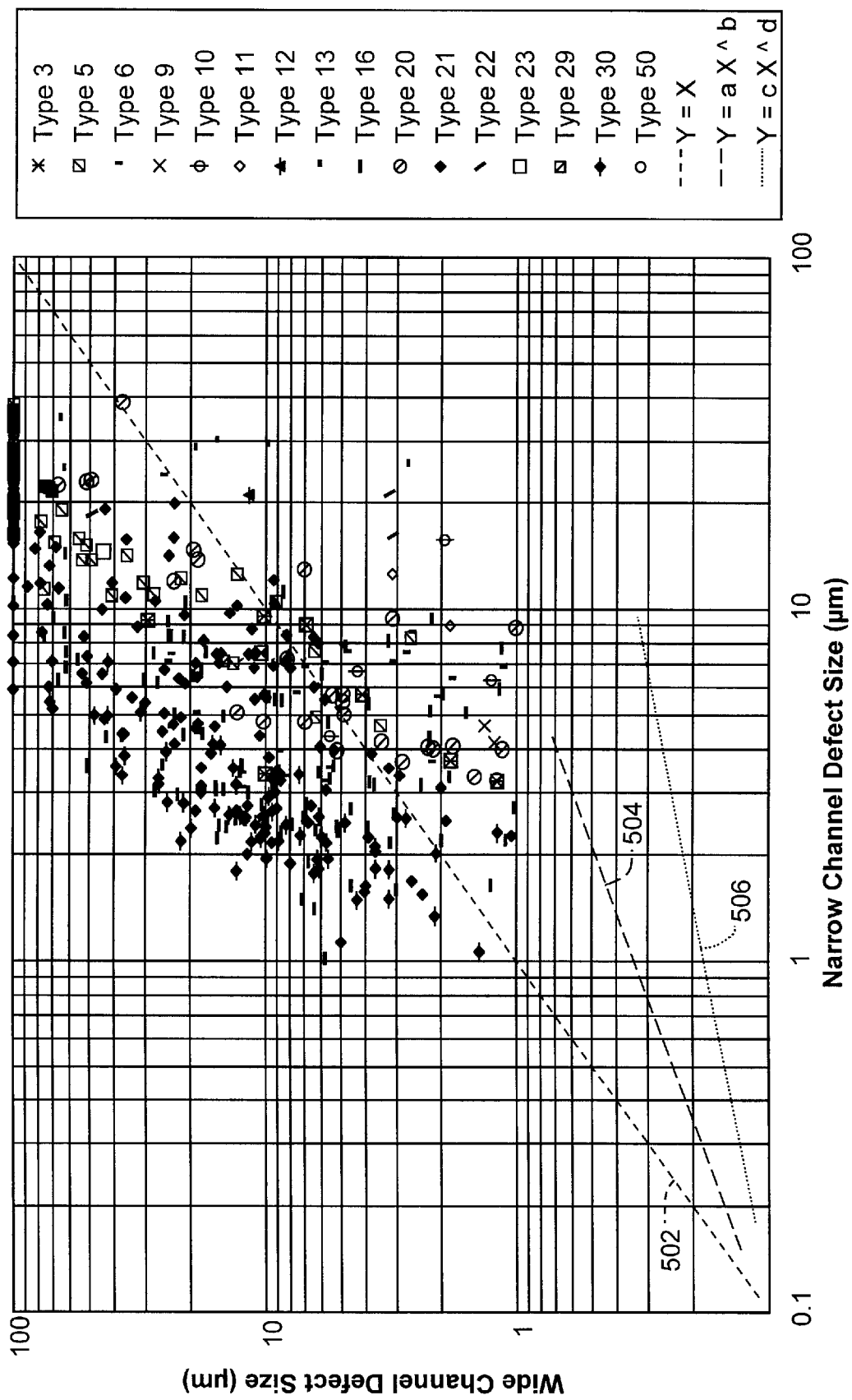
FIG. 6 is an exemplary plot of the size of a plurality of scattering events detected in the wide channel versus the size of the plurality of scattering events detected in the narrow channel, wherein the event types correspond to large defects.

FIG. 6 is an exemplary log—log plot of larger defect sizes. Unlike FIGS. 4 and 5, the size scale associated with FIG. 6 is expanded to 100 $\mu$m. As can be appreciated by FIG. 6, although there is some grouping by broad category of defect type, the same power functions (502, 504, 506) used to characterize defects between 0.1 and 10 $\mu$m do not provide accurate predictions regarding the type of relatively large defects, such as defects larger than the wavelength of the inspection laser (see FIGS. 1 and 2).

Figure 7:
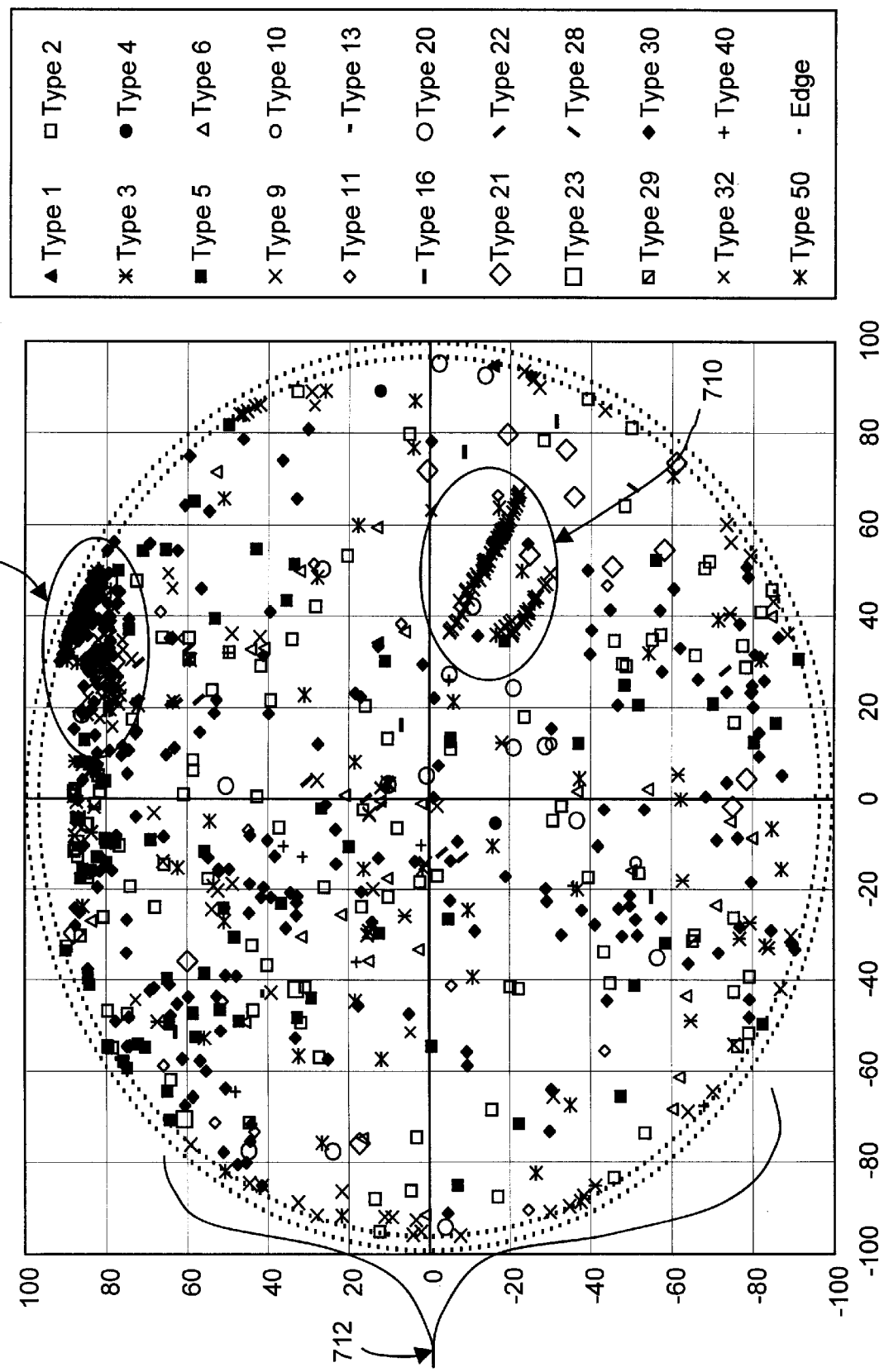
FIG. 7 is an exemplary wafer stack map illustrating defect type and location for a plurality of inspected wafers, wherein the map is generated using data that is manually gathered using microscopic defect review.
Figure 8:
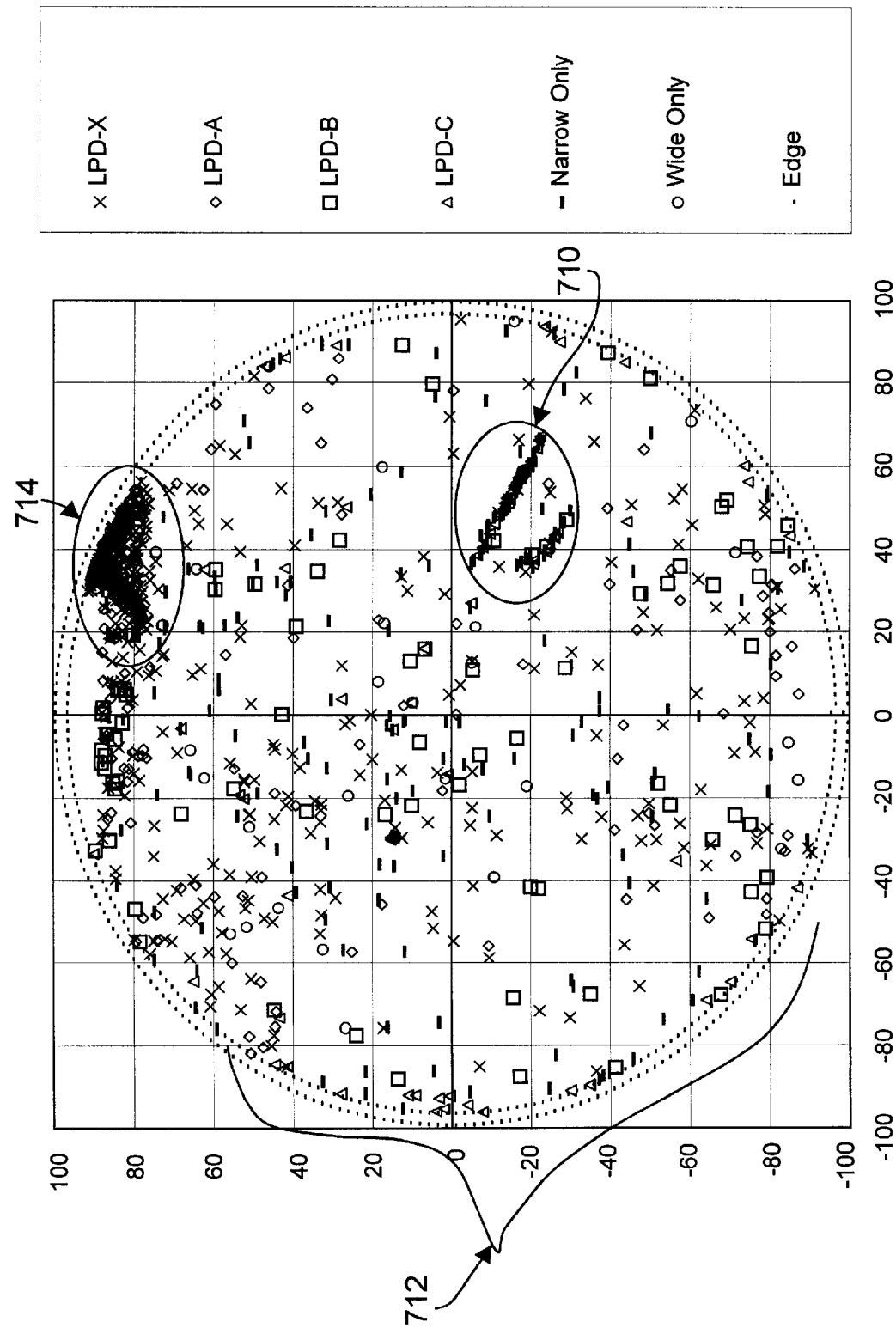
FIG. 8 is an exemplary wafer stack map similar to FIG. 7 wherein the map is generated automatically according to the invention by the wafer inspection device, without manual microscopic defect review.
Figure 9:
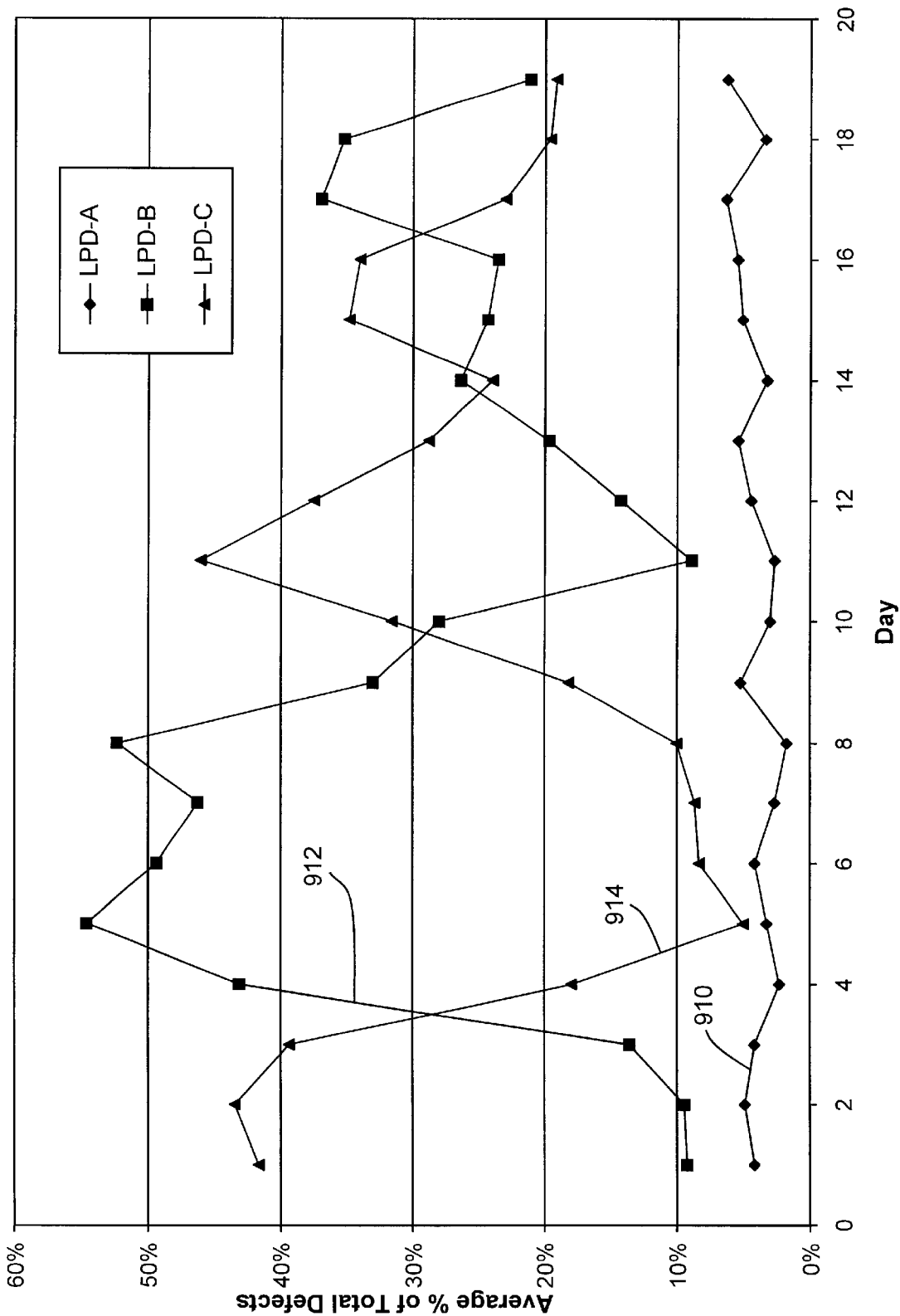
FIG. 9 is an exemplary plot of defect type and frequency data versus wafer production run.

FIGS. 7–9 illustrate, in graphic form, how knowledge of defect type can be determined and used to improve silicon wafer manufacturing efficiency and throughput. FIG. 7 is an exemplary stacked wafer map on which defects detected on 65 wafers have been plotted on a single map. FIG. 7 illustrates a stack map prepared manually, via visual inspection of a plurality of wafers. Stacked maps can be used to identify defect patterns. For example, as can be seen in FIG. 7, a pattern of substrate damage appears at approximately the 4 o'clock position (reference character 710), and around the edges of the wafers (reference character 712). Similarly, a pattern of particle defects appears as a cluster near the 1 o'clock position (reference character 714).

FIG. 8 illustrates an exemplary stack map prepared automatically in accordance with the present invention. Defects identified by the inspection device 100 (FIGS. 1 & 2) for a plurality of wafers are automatically plotted as shown. This plot may be prepared automatically by the inspection device, or by a separate computer using defect location and type data provided by the inspection device. Advantageously, therefore, using a defect type prediction, as discussed above with respect to FIG. 5, the same type of map that was manually generated in FIG. 7, may be automatically generated. As can be appreciated by comparing FIG. 8 to FIG. 7, the same types of defect patterns/groupings that were determined manually in FIG. 7 can be identified automatically. In other words, essentially the same patterns of substrate damage 710, 712, and particle defects 714 are identified automatically.

As can now be appreciated, information regarding defect type—LPD-A, LPD-B, LPD-C, and LPD-X—an be analyzed to improve efficiency, productivity, and/or throughput. FIG. 9 illustrates an exemplary plot of defect type versus production day. This information provides insight as to problems and potential problems associated with the crystal growth process and/or the epitaxial process. For example, from day 5 to day 8, and again from day 14 to day 19, the inspection process detected a relatively large number of epitaxial faults (LPD-B). Similarly, the quality of the substrate varied over the time period monitored, as shown by the number of substrate related faults (LPD-C). The number of particle faults (LPD-A), however, remained relatively steady.

Figure 10B:
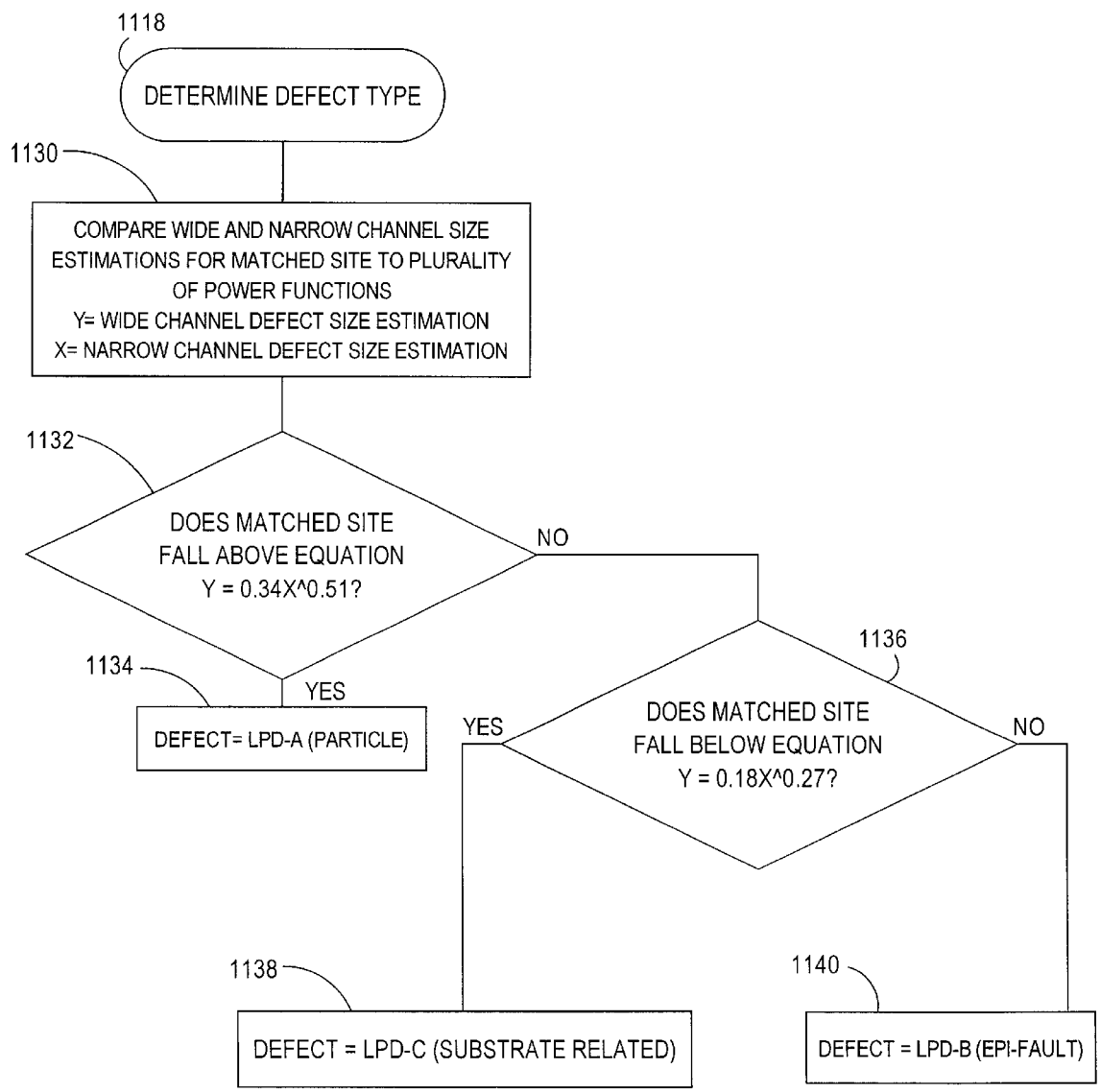

FIGS. 10A–D are flow charts of a method of inspecting a semiconductor wafer and identifying defects, according to the present invention. As shown in FIG. 10A, at step 1102, the wafer to be inspected is loaded into an inspection device or inspection chamber, such as, for example, the SP1 from KLA-Tencor. At step 1104 a laser light source 102 (FIG. 1) illuminates the surface of the wafer. As discussed above, a defect-free wafer approximates a perfect reflector and the laser light is reflected back out of the system. As shown at steps 1106 and 1110, however, if a defect is present on the wafer surface, the defect causes the laser light to scatter. The scattered laser light is preferably collected in parallel by photomultiplier tubes PMT 1 and PMT 2 (steps 1106 and 1110). PMT 1 collects light scattered between 25 and 70 degrees (see FIG. 2). Thus, PMT 1 is referred to as the wide collection channel or the wide channel. PMT 2 collects light scattered between 5 and 20 degrees. PMT 2 is referred to as the narrow collection channel or the narrow channel. When PMT 1 or PMT 2 detect a defect (by the presence of scattered light), the location of the defect is stored by the inspection device. Further, as shown at steps 1108 and 1112, each channel (wide and narrow) provides a signal (see reference characters 204, 206 in FIG. 2) indicative of the estimated size of the defect that caused the light to scatter. Such size estimation may be achieved by comparing the wide and narrow channel information to stored calibration curves/data. In the embodiment illustrated in FIG. 10A, the raw reflection data is preferably gathered in parallel (steps 1106, 1108, 1110, and 1112). A processor associated with the inspection device thereafter processes/analyzes the raw data, as processing time permits, to provide defect size and type estimations. It should be appreciated, however, that sequential data collection and processing is also possible with the present invention.

Figure 10C:
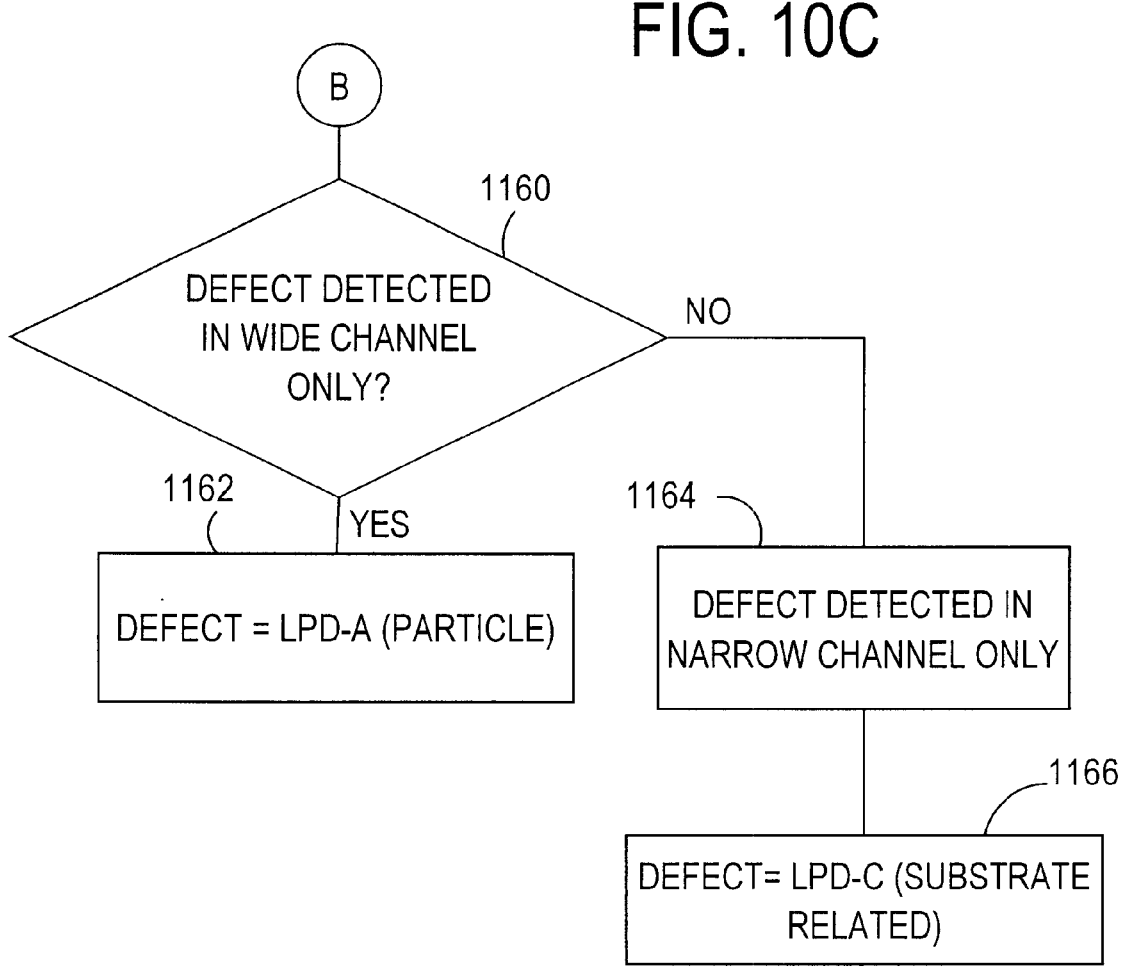

Referring to FIGS. 10A and 10C, at steps 1113 and 1114 the system determines whether a defect was detected in both the wide and narrow channel. If a defect is detected in one channel only, the method proceeds to step 1160. If it is determined at step 1160 that only the wide channel detected the defect, the defect is determined to most likely be a particle, as illustrated by step 1162. If, however, the defect is detected in the narrow channel only, the defect is most likely a substrate related defect, as shown at steps 1164 and 1166.

Figure 10D:
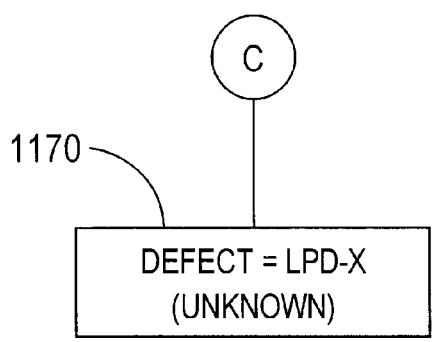

Referring now to FIGS. 10A and 10D, when a defect is detected by both channels (referred to above as a "matched site"), the method determines at step 1116 whether the detected defect saturates the wide channel. As shown at step 1170, if the defect reflects sufficient energy to saturate the wide channel, it is determined to be a defect of an unknown type.

Returning to FIG. 10A, as mentioned above, after a defect has been detected (steps 1106, 1108, 1110, and 1112), the system begins data analysis as processing time permits. In order to improve throughput, the inspection device continues to inspect the wafer surface as the data analysis proceeds, thus the system rotates and translates the wafer to illuminate another portion of the wafer surface (step 1120), and repeats the inspection process until the wafer surface has been fully inspected (step 1122).

FIG. 10B illustrates a preferred method of determining defect type (step 1118 of FIG. 10A) on the basis of the wide and narrow size information gathered for matched sites. The defect size information detected by the wide and narrow channels may be represented in Cartesian form as described at step 1130, and as described above with respect to the log—log plot shown in FIG. 5. More Particularly, the size information gathered in the wide channel (e.g., the Y axis data) is compared to the size information gathered in the narrow channel (e.g., the X axis data). At steps 1132, 1134, 1136, 1138, and 1139, the size data for a matched site is compared to a plurality of functions (e.g., equations 3 and 4 above). It should be recalled that the preferred functions are power functions that have been determined empirically by analyzing manually gathered defect data.

As discussed above with respect to FIG. 5, a defect that has size data located in the region lying above the power function defined by equation 3 is most likely a particle defect (LPD-A). A defect having size data located in the region below the power function defined by equation 4 is most likely a substrate related defect (LPD-C). A defect having size information located in the region between the power functions defined by equations 3 and 4 is most likely an epitaxial defect (LPD-B). The location and type of each detected defect is stored in memory for later use. As can now be appreciated, therefore, by determining a relevant set of power functions, a process may be devised to classify defects into at least four categories: particle defects, epitaxial defects, substrate related defects, and unknown defects.

It is to be understood that the steps described herein are not to be construed as necessarily requiring their performance in the particular order discussed or illustrated. It is also to be understood that additional or alternative steps may be employed with the present invention. In this regard, the specific and exemplary values identified herein are illustrative and should not be read in any limiting sense. Further, the exemplary power functions illustrated herein may be modified without detracting from the invention. Advantageously, the systems and methods disclosed and described herein can be implemented using readily available hardware. The software of SP1 inspection system, for example, may be modified to perform all or part of the methods disclosed herein. Further, data generated by the inspection system may be stored on a PC or similar computer for concurrent or subsequent analysis.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A method of inspecting a workpiece surface, said method comprising:

providing a workpiece having a surface to be inspected;

illuminating the workpiece surface with an energy beam, said energy beam illuminating the workpiece surface at an angle of incidence and reflecting off of the workpiece surface;

collecting in a first collector a first portion of the energy beam reflected off of the workpiece surface at a first collection angle;

collecting in a second collector a second portion of the energy beam reflected off of the workpiece surface at a second collection angle;

determining a first size characterization of a defect associated with the workpiece surface;

determining a second size characterization of the defect associated with the workpiece surface; and determining a defect type characterization by comparing the first and the second size characterizations to a plurality of logarithmic functions, said logarithmic functions being selected to identify at least three defect types.

2. A method of inspecting a workpiece surface, said method comprising:

providing a workpiece having a surface to be inspected;

illuminating the workpiece surface with an energy beam, said energy beam illuminating the workpiece surface at an angle of incidence and reflecting off of the workpiece surface;

collecting in a first collector a first portion of the energy beam reflected off of the workpiece surface at a first collection angle;

collecting in a second collector a second portion of the energy beam reflected off of the workpiece surface at a second collection angle;

determining a first size characterization of a defect associated with the workpiece surface;

determining a second size characterization of the defect associated with the workpiece surface; and determining a defect type characterization by comparing the first and the second size characterizations to a plurality of functions, said functions being selected to identify at least three defect types;

wherein the first and second size characterization determining steps comprise:

determining a first energy intensity associated with the first portion of the energy beam reflected off of the workpiece surface at the first collection angle;

determining a second energy intensity associated with the second portion of the energy beam reflected off of the workpiece surface at the second collection angle;

identifying the first size estimation of the defect associated with the workpiece surface by comparing the first determined energy intensity to a reference standard; and identifying the second size estimation of the defect associated with the workpiece surface by comparing the second determined energy intensity to the reference standard.

3. The method of claim 2 wherein the workpiece comprises a silicon wafer.

4. The method of claim 3 wherein the first collector comprises a first photomultiplier tube and the second collector comprises a second photomultiplier tube.

5. The method of claim 3 wherein the energy beam comprises a laser beam.

6. The method of claim 3 wherein:

the workpiece surface is generally planar;

the angle of incidence is substantially normal to the generally planar workpiece surface;

the first collection angle comprises a 25 degree to 70 degree collection angle; and the second collection angle comprises a 5 to 20 degree collection angle, said first and second collection angles being measured relative to the angle of incidence of the energy beam.

7. The method of claim 3 wherein the plurality of functions comprise two power functions.

8. The method of claim 7 wherein the two power functions are defined by the equations:

$$Y=aX^b; \text{ and}$$

$$Y=cX^d;$$

where a and b are parameters selected to define a region associated with particle defects; and c and d are parameters selected to define a region associated with substrate related defects.

9. The method of claim 8 wherein:

a=0.34;

b=0.51;

c=0.18; and d=0.27.

10. The method of claim 8 further comprising:

determining a first value of Y, said first value of Y being determined by the equation $Y=aX^b$ with X being equal to the second size characterization;

comparing the determined first value of Y to the first size characterization;

determining a second value of Y, said second value of Y being determined by the equation $Y=cX^d$ with X being equal to the second size estimation;

comparing the determined second value of Y to the first size characterization;

determining the defect type to be a particle defect if the first size characterization is greater than the first value of Y;

determining the defect type to be a substrate related defect if the first size characterization is less than the second value of Y; and determining the defect type to be an epitaxial defect if the first size characterization is less than the first value of Y and greater than the second value of Y.

11. The method of claim 10 wherein:

a=0.34;

b=0.51;

c=0.18; and d=0.27.

12. A method of inspecting a workpiece surface, said method comprising:

providing a workpiece having a surface to be inspected;

illuminating the workpiece surface with an energy beam, said energy beam illuminating the workpiece surface at an angle of incidence and reflecting off of the workpiece surface;

collecting in a first collector a first portion of the energy beam reflected off of the workpiece surface at a first collection angle;

collecting in a second collector a second portion of the energy beam reflected off of the workpiece surface at a second collection angle;

determining a first size characterization of a defect associated with the workpiece surface;

determining a second size characterization of the defect associated with the workpiece surface; and determining a defect type characterization by comparing the first and the second size characterizations to a plurality of functions, said functions being selected to identify at least three defect types calibrating the first and second size characterizations by:

providing a defect free workpiece having a plurality of calibration particles having predetermined geometric shapes and sizes placed on a surface of the defect free workpiece;

illuminating the surface of the defect free workpiece with the energy beam;

scattering the energy beam off of the plurality of calibration particles;

determining a first size calibration value for each of the plurality of calibration particles by measuring an intensity of a portion of the scattered energy beam collected in the first collector;

comparing the first size calibration value of each of the plurality of calibration particles to the predetermined size of the calibration particle;

determining a first calibration curve based on the comparison of the first size calibration value of each of the plurality of calibration particles to the predetermined size of the calibration particle, whereby the first size characterization is determined by comparing an intensity of the first portion of the energy beam reflected off of the workpiece surface at the first collection angle to the first calibration curve;

determining a second size calibration value for each of the plurality of calibration particles by measuring an intensity of a portion of the scattered energy beam collected in the second collector;

comparing the second size calibration value of each of the plurality of calibration particles to the predetermined size of the calibration particle; and determining a second calibration curve based on the comparison of the second size calibration value of each of the plurality of calibration particles to the predetermined size of the calibration particle, whereby the second size characterization is determined by comparing an intensity of the second portion of the energy beam reflected off of the workpiece surface at the second collection angle to the second calibration curve.

13. A method of inspecting a workpiece having a workpiece surface, said method comprising:
   placing the workpiece in an inspection chamber, said inspection chamber comprising a light generator generating a light beam, a first beam collector, and a second beam collector;
   illuminating the surface of the workpiece with the light beam, said light beam illuminating the surface at an angle of incidence;
   reflecting the light beam off of a defect associated with the surface of the workpiece;
   collecting in the first beam collector a portion of the reflected light beam that is reflected in a first collection angle;
   collecting in the second beam collector a portion of the reflected light beam that is reflected in a second collection angle;
   determining a first reflection intensity signal representative of an intensity of the portion of the reflected light beam that is reflected in the first collection angle;
   determining a second reflection intensity signal representative of an intensity of the portion of the reflected light beam that is reflected in the second collection angle; and
   characterizing the defect associated with the surface of the workpiece by comparing the first and second reflection intensity signals to a plurality of logarithmic functions.

14. The method of claim 13 wherein the first and second reflection intensity signal determining steps comprise:
   determining a first energy intensity associated with the first portion of the energy beam reflected off of the workpiece surface at the first collection angle;
   determining a second energy intensity associated with the second portion of the energy beam reflected off of the workpiece surface at the second collection angle;
   identifying the first size estimation of the defect associated with the workpiece surface by comparing the first determined energy intensity to a reference standard; and
   identifying the second size estimation of the defect associated with the workpiece surface by comparing the second determined energy intensity to the reference standard.

15. A system for identifying a type of defect associated with a workpiece having a workpiece surface, said system comprising:
   a light generator generating a light beam, said light beam being directed to and reflecting off of the defect;
   a first beam collector positioned to receive a first portion of the light beam reflected off of the defect, said first portion being reflected off of the defect at a first collection angle, said first beam collector providing a first intensity signal having a parameter representative of an intensity of the first portion;
   a second beam collector positioned to receive a second portion of the light beam reflected off of the defect, said second portion being reflected off of the defect at a second collection angle, said second beam collector providing a second intensity signal having a parameter representative of an intensity of the second portion; and
   a processor determining the type of defect by comparing the first and second intensity signals to a plurality of functions, said functions being selected to identify at least three defect types, wherein the processor determines a first defect size estimation as a function of the first intensity signal and a second defect size estimation as a function of the second intensity signal.

16. The system of claim 15 wherein the workpiece comprises a silicon wafer.

17. The system of claim 16 wherein the light generator comprises a laser and wherein the light beam comprises a laser beam.

18. The system of claim 16 wherein the first beam collector comprises a first photomultiplier tube, and the second beam collector comprises a second photomultiplier tube.

19. The system of claim 16 further comprising a cylindrical elliptical mirror being positioned to focus the first portion of the light beam reflected off of the defect into the first beam collector at the first collection angle, and wherein the first collection angle comprises a 25 degree to 70 degree collection angle, and the second collection angle comprises a 5 degree to 20 degree collection angle.

20. The system of claim 15 wherein the plurality of functions comprise two power functions defined by the equations:

$$Y=aX^b$$

$$Y=cX^d$$

where
   Y is a function variable associated with the first defect size estimation and X is a function variable associated with the second defect size estimation;
   a and b are parameters selected to define a first defect region associated with particle defects such that detected defects having first and second defect size estimations falling in the first defect region are determined by the processor to be particle defects;
   c and d are parameters selected to define a second defect region associated with substrate related defects such that the detected defects having first and second size estimations falling in the second defect region are determined by the processor to be substrate related defects; and
   wherein a third defect region is defined between the first and second defect regions, said third defect region being associated with epitaxial defects such that the detected defects having first and second size estimations falling the third defect region are determined by the processor to be epitaxial defects.

21. The system of claim 20 wherein:
   a=0.34;
   b=0.51;
   c=0.18; and
   d=0.27.

22. A method of inspecting semiconductor wafer surfaces, said method comprising:
   locating a plurality of defects associated with the wafer surfaces;
   estimating a first size associated with each of the plurality of defects;
   estimating a second size associated with each of the plurality of defects;

creating a plot of the first size estimation versus the second size estimation;

analyzing the plurality of defects to determine a defect type associated with each of the plurality of defects;

identifying on the plot the defect type associated with each of the plurality of defects; and locating on the plot at least two curves that substantially separates the plurality of defects into at least three different defect types;

wherein the first and second size estimating steps comprise:

determining a first energy intensity associated with the first portion of the energy beam reflected off of the workpiece surface at the first collection angle;

determining a second energy intensity associated with the second portion of the energy beam reflected off of the workpiece surface at the second collection angle;

identifying the first size estimation of the defect associated with the workpiece surface by comparing the first determined energy intensity to a reference standard; and identifying the second size estimation of the defect associated with the workpiece surface by comparing the second determined energy intensity to the reference standard.

\* \* \* \* \*

UNITED STATES PATENT AND TRADEMARK OFFICE
CERTIFICATE OF CORRECTION

PATENT NO. : 6,515,742 B1
DATED : February 4, 2003
INVENTOR(S) : David John Ruprecht It is certified that error appears in the above-identified patent and that said Letters Patent is hereby corrected as shown below:

<u>Title page,</u>
Item [73], Assignee, "MEMC Electronic Materials, Inc., St. Peters, MI (US)" should read -- MEMC Electronic Materials, Inc., St. Peters, MO (US) --.

Signed and Sealed this

Twenty-fourth Day of June, 2003

JAMES E. ROGAN
*Director of the United States Patent and Trademark Office*